United States Patent [19]

Thalhammer et al.

[11] Patent Number: 5,208,351

[45] Date of Patent: May 4, 1993

[54] PROCESS FOR THE PREPARATION OF N-CYANOIMIDOCARBONATES

[75] Inventors: Franz Thalhammer; Stefan Weiss, both of Trostberg, Fed. Rep. of Germany

[73] Assignee: SKW Trostberg Aktiengesellschaft, Trostberg, Fed. Rep. of Germany

[21] Appl. No.: 914,268

[22] Filed: Jul. 15, 1992

[30] Foreign Application Priority Data

Jul. 17, 1991 [DE] Fed. Rep. of Germany ....... 4123608

[51] Int. Cl.$^5$ ................. C07D 317/32; C07D 319/06; C07D 249/00
[52] U.S. Cl. ....................................... 549/449; 558/9; 549/371
[58] Field of Search ...................... 549/449, 371; 558/9

[56] References Cited

U.S. PATENT DOCUMENTS 4,298,544 11/1981 Robinson ...................... 549/449 X

OTHER PUBLICATIONS

A. Hantesch & M. Wolvekamp; Justus Liebigs Ann. Chem., 331, 265 (1904).

Primary Examiner—Marianne M. Cintins
Assistant Examiner—Michael B. Hydorn
Attorney, Agent, or Firm—Felfe & Lynch

[57] ABSTRACT

The present invention provides a process for the preparation of N-cyanoimidocarbonates of the general formula:

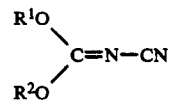

in which $R^1$ and $R^2$ are the same and are alkyl radicals containing up to 4 carbon atoms or $R^1$ and $R^2$ are joined together to give an ethylene or propylene chain which is optionally substituted by an alkyl radical containing up to 3 carbon atoms, wherein an imidocarbonate obtained in aqueous alkaline solution from the appropriate alcohol and cyanogen chloride is added with an acid to an aqueous solution of cyanamide in such a manner that the reaction mixture has a pH value of from 3 to 8.

23 Claims, No Drawings

PROCESS FOR THE PREPARATION OF N-CYANOIMIDOCARBONATES

FIELD OF THE INVENTION

The present invention is concerned with a process for the preparation of substituted N-cyanoimidocarbonates from cyanogen chloride, alcohols and cyanamide.

BACKGROUND OF THE INVENTION

Dialkyl-N-cyanoimidocarbonates are valuable synthesis components for the preparation of substituted cyanoguanidine compounds. In this way, by means of successive substitution of the alkoxy radicals, it is also possible to obtain asymmetrically substituted cyanoguanidine compounds, which can be used, inter alia, as histamine 2H antagonists.

In many cases, dialkyl-N-cyanoimidocarbonates can replace previously employed reagents, such as dimethyl-N-cyanoimidodithiocarbonates (see J. Org. Chem., Vol. 39, No. 11, 1522 et seq./1974) or diphenyl-N-cyanoimidocarbonate, whereby the formation of by-products which are difficult to deal with and/or dangerous to health are avoided and improved yields are obtained.

The synthesis of diethyl N-cyanoimidocarbonate by the reaction of isolated diethyl imidocarbonate with cyanamide under anhydrous conditions has already been described (see Chem. Ber., 100, 2604/1967). In this case, a yield of only 69% of crude product was obtained which, for purification, has to be recrystallised from anhydrous diethyl ether.

In EP 0 014 064 B1, there is described a process for the preparation of disubstituted dimethyl or diethyl N-cyanoimidocarbonates by the reaction of an appropriately substituted imidocarbonate with cyanamide in a two-phase system which contains water and an organic solvent which is not miscible with water, for example toluene.

In DE-OS 32 25 249, there is described a process according to which sodium cyanide is reacted under alkaline conditions with an appropriate alcohol, subsequently chlorine is passed in and, after neutralisation of the reaction mixture and addition of cyanamide, the substituted N-cyanoimidocarbonate formed is, after the addition of methylene chloride, obtained from the organic phase.

The above-described processes suffer from the disadvantage that, in the case of the preparation, either health-endangering by-products are formed or organic solvents, some of which are chlorinated, are needed which require special expense for the removal thereof after the reaction has taken place.

OBJECTS OF THE INVENTION

Consequently, there is a need to develop a process which does not suffer from the above-mentioned disadvantages and, in particular, permits the preparation of substituted N-cyanoimidocarbonates also on a large scale in an environmentally satisfactory manner.

DESCRIPTION OF THE INVENTION

Thus, according to the present invention, there is provided a process for the preparation of N-cyanoimidocarbonates of the general formula:

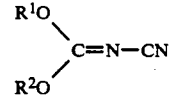

wherein $R^1$ and $R^2$ are the same and are alkyl radicals containing up to 4 carbon atoms or $R^1$ and $R^2$ are joined together to give an ethylene or propylene chain which is optionally substituted by an alkyl radical containing up to 3 carbon atoms, which is characterised in that an imidocarbonate obtained in aqueous alkaline solution from the appropriate alcohol and cyanogen chloride is added with an acid to an aqueous solution of cyanamide in such a manner that the reaction mixture has a pH value of from 3 to 8.

In contradistinction to an earlier description of the process, according to the present state of the art it is also possible safely to use cyanogen chloride also on a large scale and to use it without danger for chemical reactions, for example for the preparation of imidocarbonates. The cyanogen chloride is advantageously passed in gaseous form into an aqueous solution of an alcohol which has been rendered alkaline by the addition of an aqueous solution of sodium hydroxide, the pH value of the solution is maintained between 8 and 14 and the temperature of the reaction mixture is maintained between $-5°$ and $35°$ C. and preferably between $10°$ and $20°$ C. Under these conditions, the cyanogen chloride reacts quickly and completely. Under these conditions, the imidocarbonate formed is, surprisingly, more stable than in a neutral medium.

For a production of imidocarbonates on a large scale, the use of technical cyanogen chloride, such as is used, for example, in the preparation of cyanuric chloride, is, on the basis of the process according to the present invention, possible without limitation. Instead of in the gaseous form, the cyanogen chloride can also be dosed into the reaction mixture in condensed or in dissolved form.

The molar ratio of aqueous sodium hydroxide solution to cyanogen chloride depends upon the purity of the cyanogen chloride used. Normally, a ratio of cyanogen chloride to aqueous sodium hydroxide solution of from 1 to 0.75 and preferably of 0.9 is employed.

The concentration of the aqueous sodium hydroxide solution can vary between 15 and 50% by weight, it being especially advantageous to use an aqueous solution of sodium hydroxide with a content of sodium hydroxide of 30% by weight.

The molar ratio for the alcohol used is 1.9 to 3.0 and preferably 2.0 to 2.1 or 1.0 to 1.5 and preferably 1.1 for diols, in each case referred to the amount of aqueous sodium hydroxide solution used.

As alcohols for the preparation of the imidocarbonate, there can be used straight- or branched-chained alcohols containing up to 4 carbon atoms or diols containing 2 or 3 carbon atoms.

The preparation of the imidocarbonate preferably takes place in a device which is suitable for introducing the cyanogen chloride in very fine division via an appropriate nozzle or a special stirrer or with the help of a static mixer into the reaction mixture. A preferred device for the preparation of the dialkylimidocarbonate is a so-called loop reactor.

It has proved to be preferable to cool the alkaline solution of the dialkyl imidocarbonate obtained and to react it further as quickly as possible.

For the preparation of the dialkyl N-cyanoimidocarbonate, it has, surprisingly, proved to be advantageous to dose the aqueous solution of the dialkyl imidocarbonate into the cyanamide solution and not, the other way round, to dose the cyanamide solution into the imidocarbonate. By means of the simultaneous addition of dilute aqueous acid, the pH value of the reaction mixture is maintained in the range of from 3 to at most 8 and preferably of from 6 to 7. In this way, higher total yields are obtained than in the case of the previously known processes.

The concentration of the cyanamide solution used can vary between 20 and 60% by weight, the use of a commercially available 50% aqueous solution being preferred. The molar amount of cyanamide, referred to the amount of aqueous sodium hydroxide solution, is from 0.7 to 1.0 and preferably 0.85 per mol equivalent of aqueous sodium hydroxide solution.

As acids, there can be used mono- or polybasic inorganic or carboxylic acids, for example hydrochloric acid, acetic acid, sulphuric acid, nitric acid or phosphoric acid, it being preferred to work with 20% hydrochloric acid.

As bases, there can be used mono- or polybasic organic or inorganic bases. It is preferred to use aqueous sodium hydroxide solution in a concentration of from 15 to 50% by weight and more preferably in a concentration of from 25 to 30% by weight of sodium hydroxide.

During the dosing in of the reaction components or during a short post-reaction time, the dialkyl N-cyanoimidocarbonate precipitates out, the crystallisation of which can be improved by cooling to a temperature below 0° C.

The isolation of the dialkyl N-cyanoimidocarbonates can take place by centrifuging or filtration or, in the case of oily products, by phase separation, whereafter the product can be washed with cold water and subsequently dried.

Depending upon the intensity of the washing, the dialkyl N-cyanoimidocarbonates obtained by the process according to the present invention can achieve a degree of purity of from 90 to 99%. The main impurity is the chemically inert sodium chloride.

By means of extraction of the mother liquor with an organic solvent, for example chloroform, methylene chloride, toluene or ethyl acetate, further amounts of dialkyl N-cyanoimidocarbonate can possibly be obtained.

By means of appropriate choice of the concentrations of the reaction components, only that amount of aqueous mother liquor is obtained which is needed for dissolving the salts formed.

The following Examples are given for the purpose of illustrating the present invention:

EXAMPLE 1

A mixture of 35.2 g (1.10 mol) technical methanol and 88.0 g (0.55 mol) of a 25% aqueous sodium hydroxide solution was cooled to 5° C. and, with external cooling, gaseous cyanogen chloride was passed in in such a manner that the internal temperature was maintained between 10° and 15° C. Upon reaching a pH value of 12.5, the introduction of cyanogen chloride was stopped. The consumption of cyanogen chloride was 31.4 g (0.51 mol). The suspension so obtained (a part of the sodium chloride formed precipitates out) was immediately thereafter pumped with 20% hydrochloric acid, but separately from one another, into a solution of 18.9 g (0.45 mol) cyanamide in 18 ml of water. The speed of addition of the two components was so adjusted that, with ice cooling, an internal temperature of 20° to 25° C. was maintained. By means of controlling the addition of acid, the pH value was kept between 6.4 and 6.7. The consumption of acid was 80.3 g (0.44 mol). The product already precipitated out during the mixing together of the reactants. The suspension was stirred for a further 20 minutes at 20° C. and then cooled for 1 hour to −5° C. The crystals obtained were filtered off with suction, washed twice with, in each case, 10 ml of cold water and dried in a vacuum at ambient temperature. 42.1 g (0.37 mol=82.0% of theory) of colourless crystals were obtained with a melting point of 63.2° C. The purity of the dimethyl N-cyanoimidocarbonate obtained was more than 99%. By means of extraction of the mother liquor and wash water with 100 ml methylene chloride, it was possible to obtain a further 5.9 g (0.052 mol) of product with a melting point of 53°–56° C. Thus, the total yield was 93.3%.

EXAMPLE 2

11.6 g (0.19 mol) gaseous cyanogen chloride were passed into a mixture of 21.2 g (0.46 mol) ethanol and 28.0 g (0.21 mol) 30% aqueous sodium hydroxide solution in such a manner that the temperature did not exceed 5° C. Upon reaching a pH value of 12.5, the addition was stopped and the solution of diethyl imidocarbonate thus obtained was added dropwise to 15.1 g (0.18 mol) of a 50% solution of cyanamide with the simultaneous addition of 20% hydrochloric acid. By means of external cooling, a temperature of 15° to 20° C. was maintained and the addition of acid (in all 28.3 g, 0.16 mol) was so controlled that a pH value of 6.4 to 6.6 was maintained. After stirring for 1 hour at ambient temperature, the phases were separated and the pale yellow organic phase was shaken out twice with, in each case, 10 ml of water. The diethyl N-cyanoimidocarbonate was obtained as a yellowish oil in a yield of 15.2 g (0.107 mol=59% of theory).

EXAMPLE 3

While cooling with ice, 11.6 g (0.19 mol) cyanogen chloride was passed into a mixture of 13.6 g (0.22 mol) ethylene glycol and 33.6 g (0.21 mol) 25% aqueous sodium hydroxide solution at such a rate that the temperature did not exceed 10° C. Upon reaching a pH value of 12.4, the addition was stopped and the reaction mixture was further stirred for 15 minutes at 10° C. With control of the pH value (6.4 to 6.6), the solution obtained was added dropwise at 20° to 25° C., with the simultaneous addition of 21.4 g (0.12 mol) of 20% aqueous hydrochloric acid, to an aqueous, commercially available solution of 7.6 g (0.18 mol) cyanamide in 7.5 ml of water, the reaction mixture was stirred for 30 minutes at ambient temperature and then cooled to −5° C. 9.62 g (85.9 mol=48% of theory) of colourless crystals were thereby obtained with a melting point of 74° to 77° C. which were filtered off with suction and dried and identified as being 0,0′-ethylene-N-cyanoimidocarbonate.

EXAMPLE 4

Analogously to Example 1, there were used 16.0 g (0.5 mol) methanol, 41.4 g (0.21 mol) 20.3% aqueous sodium hydroxide solution and 12.3 g (0.20 mol) cyanogen chloride. In the second step, 14.6 g (0.18 mol) of a 50% cyanamide solution was used and 32.3 g (0.18 mol) of 20% hydrochloric acid consumed. Without washing with water, 16.6 g. of product were obtained with a melting point of 58° to 62.5° C. and a purity of 94.6%. The chloride content was 3.0%. By means of extraction of the mother liquor with 40 ml methylene chloride, there were obtained a further 3.3 g of product with a melting point of 56° to 58° C. and a purity of 88.8%. The total yield was 90.4%, referred to the cyanamide.

EXAMPLE 5

1100 g (16.6 mol) cyanogen chloride (technical grade, 93%) were passed in gaseous form into a solution of 1216 g (38.0 mol) methanol (technical grade) and 2857 g (20.0 mol) 28.7% aqueous sodium hydroxide solution in such a manner that the temperature was maintained between 10° and 20° C. Upon reaching a pH value of 12.0, the introduction of the cyanogen chloride was stopped. This solution was pumped into 1260 g (15.0 mol) of a 50% solution of cyanamide in such a manner that, in the case of the simultaneous addition of 2762 g (14.0 mol) of 18% hydrochloric acid, the temperature was maintained by cooling at 20° to 25° C. and the pH value at 6.4 to 6.6. The suspension obtained was cooled to 0° C., filtered off with suction and the filter cake washed twice with, in each case, 1000 ml of cold water. After drying at 35° C. in a vacuum (100 mbar), there were obtained 1426 g of colourless product with a melting point of 61° to 63° C. The analysis gave a purity of 99.4% and the chloride content was 0.2%.

EXAMPLE 6

17.7 g (0.29 mol) cyanogen chloride were condensed at −3° C. and, while cooling to 10° C. to 15° C., added dropwise to a solution of 40.0 g (0.30 mol) of a 30% aqueous sodium hydroxide solution and 18.4 g (0.58 mol) methanol. A pH value of 11.8 was thereby obtained. The solution obtained of dimethyl imidocarbonate was added dropwise, simultaneously with 37 g (0.2 mol) of a 20% hydrochloric acid, to 19.3 g (0.23 mol) of a 50% cyanamide solution in such a manner that the temperature of the reaction mixture did not exceed 20° C. and the pH value was between 5.9 and 6.6. The precipitated product was, after cooling for 90 minutes at 0° C., filtered off with suction and dried without washing. There were thereby obtained 25.5 g of crystals with a melting point of 52° to 55° C. and a purity of 93.8%. The yield of pure product was 91.3%.

We claim:
1. Process for the preparation of N-cyanoimidocarbonates of the general formula:

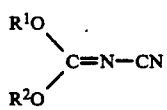

in which $R^1$ and $R^2$ are the same and are alkyl radicals containing up to 4 carbon atoms or $R^1$ and $R^2$ are joined together to give an ethylene or propylene chain which is optionally substituted by an alkyl radical containing up to 3 carbon atoms, wherein an imidocarbonate obtained in aqueous alkaline solution from the appropriate alcohol and cyanogen chloride is added with an acid to an aqueous solution of cyanamide in such a manner that the reaction mixture has a pH value of from 3 to 8.

2. Process according to claim 1, wherein the reaction between the alcohol and the cyanogen chloride is carried out in aqueous alkaline solution at a temperature of from −5° to 35° C. and the pH value of the solution is maintained between 8 and 14.

3. Process according to claim 2, wherein the reaction between the alcohol and the cyanogen chloride is carried out at a temperature of from 10° to 20° C.

4. Process according to claim 1, wherein the imidocarbonate present in solution is, immediately after its preparation, dosed simultaneously with aqueous hydrochloride acid into an aqueous solution of cyanamide in such a manner that the temperature of the reaction mixture is maintained within the limits of 10° to 30° C. and a pH range of from 3 to 8 is maintained.

5. Process according to claim 4, wherein the temperature of the reaction mixture is maintained at about 20° C.

6. Process according to claim 4, wherein the pH value is maintained at 6 to 7.

7. Process according to claim 1, wherein $R^1$ and $R^2$ are methyl or ethyl radicals.

8. Process according to claim 1, wherein $R^1$ and $R^2$ together signify an ethylene chain.

9. Process according to claim 1, wherein the amount of cyanogen chloride is 0.75 to 1 mol per mol equivalent of base.

10. Process according to claim 9, wherein the amount of cyanogen chloride is 0.9 mol per mol equivalent of base.

11. Process according to claim 1, wherein gaseous cyanogen chloride is used.

12. Process according to claim 1, wherein the molar amount of alcohol used is 1.9 to 3.0, referred to the mol equivalent of base used.

13. Process according to claim 12, wherein the molar amount of alcohol used is 2.0 to 2.1, referred to the mol equivalent of base used.

14. Process according to claim 1, wherein the molar amount of diol used is 1.0 to 1.5, referred to the mol equivalent of base used.

15. Process according to claim 14, wherein the molar amount of diol used is 1.1, referred to the mol equivalent of base used.

16. Process according to claim 1, wherein, as cyanamide component, there is used a commercially-available 20 to 60% aqueous cyanamide solution in an amount of from 0.7 to 1 mol per mol equivalent of base used.

17. Process according to claim 16, wherein the aqueous cyanamide solution is used in an amount of 0.85 mol per mol equivalent of base used.

18. Process according to claim 1, wherein 10 to 35% hydrochloric acid is used as acid.

19. Process according to claim 1, wherein, as base, there is used an aqueous solution of sodium hydroxide in a concentration of 15 to 50% by weight.

20. Process according to claim 19, wherein, as base, there is used an aqueous solution of sodium hydroxide in a concentration of 25 to 30% by weight.

21. Process according to claim 1, wherein the N-cyanoimidocarbonate is crystallized from the aqueous mother liquor by cooling to a temperature below 0° C. and isolated by means of conventional processes.

22. Process according to claim 21, wherein further product is obtained by extraction of the mother liquor with an organic solvent.

23. Process according to claim 22, wherein the organic solvent used is methylene chloride.

* * * * *